US008946262B2

(12) United States Patent
Christ et al.

(10) Patent No.: US 8,946,262 B2
(45) Date of Patent: Feb. 3, 2015

(54) METHODS OF PREVENTING AND TREATING GASTROINTESTINAL DYSFUNCTION

(75) Inventors: David D Christ, Newark, DE (US); Bruce A Wallin, Haverford, PA (US); Deanne D Garver, Downingtown, PA (US); William K Schmidt, Davis, CA (US); David Jackson, Cape Coral, FL (US)

(73) Assignee: Adolor Corporation, Lexington, MA (US)

( * ) Notice: Subject to any disclaimer, the term of this patent is extended or adjusted under 35 U.S.C. 154(b) by 1901 days.

(21) Appl. No.: 10/999,054

(22) Filed: Nov. 29, 2004

(65) Prior Publication Data

US 2005/0124657 A1 Jun. 9, 2005

Related U.S. Application Data

(60) Provisional application No. 60/526,851, filed on Dec. 4, 2003.

(51) Int. Cl.
| | | |
|---|---|---|
| *A01N 43/40* | (2006.01) |
| *A61K 31/445* | (2006.01) |
| *A01N 37/00* | (2006.01) |
| *A61K 31/185* | (2006.01) |
| *A61K 31/135* | (2006.01) |
| *A01N 31/00* | (2006.01) |
| *A61K 31/045* | (2006.01) |
| *A01N 37/18* | (2006.01) |
| *A61K 31/16* | (2006.01) |

(52) U.S. Cl.
CPC .................................. *A61K 31/445* (2013.01)
USPC ........... 514/315; 514/317; 514/576; 514/613; 514/646; 514/730

(58) Field of Classification Search
USPC ......... 514/282, 295, 315, 317, 576, 613, 646, 514/730
See application file for complete search history.

(56) References Cited

U.S. PATENT DOCUMENTS

| 4,176,186 | A | 11/1979 | Goldberg et al. | 424/260 |
|---|---|---|---|---|
| 4,581,456 | A | 4/1986 | Barnett | 546/185 |
| 4,987,126 | A | 1/1991 | Bargiotti et al. | 514/34 |
| 5,159,081 | A | 10/1992 | Cantrell et al. | 546/226 |
| 5,250,542 | A | 10/1993 | Cantrell et al. | 514/315 |
| 5,270,328 | A | 12/1993 | Cantrell et al. | 514/331 |
| 5,434,171 | A | 7/1995 | Frank et al. | 514/331 |
| 5,972,954 | A | 10/1999 | Foss et al. | 514/282 |
| 6,451,806 | B2 | 9/2002 | Farrar | 514/282 |
| 6,469,030 | B2 * | 10/2002 | Farrar et al. | 514/331 |
| 2001/0036951 | A1 * | 11/2001 | Farrar et al. | 514/326 |
| 2001/0047005 | A1 * | 11/2001 | Farrar | 514/282 |

OTHER PUBLICATIONS

Schmidt, W. K. (The American Journal of Surgery, 2001, 182 (Suppl. to Nov. 2001), 27S-38S.*
Schmidt, W. K. (The American Journal of Surgery: 2001, 182, 27S-38S published on Nov. 2001).*
Zimmerman et al. (Drugs of the Future, 1994, 19: 1078-1083).*
Bagnol, D., et al., "Cellular localization and distribution of the cloned MU and KAPPA opioid receptors in rat gastrointestinal tract," *Neuroscience*, 1997, 81(2), 579-591.
Bagnol, D., "Changes in enkephalin immunoreactivity of sympathetic ganglia and digestive tract of the cat after splanchnic nerve ligation," et al., *Regul. Pept.*, 1993, 47, 259-273.
Bhargava, H.N., et al., "Effect of nitric oxide synthase inhibition on tolerance to the analgesic action of D-Pen$^2$, D-Pen$^5$ enkephalin and morphine in the mouse," *Neuropeptides*, 1996, 30(3), 219-223.
Bilsky, E.J., et al., "Effects of naloxone and D-Phe-Cys-Tyr-D-Trp-Arg-Thr-Pen-Thr-NH$_2$ and the protein kinase inhibitors H7 and H8 on acute morphine dependence and antinociceptive tolerance in mice," *J. Pharmacol. Exp. Ther.*, 1996, 277(1), 484-490.
Copeland, R.E., Enzymes. A Practical Introduction to Structure, Mechanism, and Data Analysis, 2$^{nd}$ Ed., Wiley-VCH, New York, 2000, p. 88.
Dorland's Illustrated Medical Dictionary, 27$^{th}$ Ed., W.B. Saunders Co., Phila., 1988, p. 816.
Dorland's Illustrated Medical Dictionary, 27$^{th}$ Ed., W.B. Saunders Co., Phila., 1988, p. 375.
Dourish, C.T., et al., "Enhancement of morphine analgesia and prevention of morphine tolerance in the rat by the cholecystokinin antagonist L-364,718," *Eur. J. Pharmacol.*, 1988, 147, 469-472.
Koch, T.R., et al., "Inhibitory neuropeptides and intrinsic inhibitory innervation of descending human colon," *Digestive Diseases and Sciences*, 1991, 36, 712-728.
Kreek, M.J., et al., "Naloxone, a specific opioid antagonist, reverses chronic idiopathic constipation," *J. Lancet*, 1983, 261-262.
Livingston, E.H., et al., "Postoperative Ileus," *Digestive Diseases and Sciences*, 1990, 35(1), 121-132.
Mack, D.J., et al., "Paralytic ileus: response to naloxone," *Br. J. Surg.*, 1989, 76(10), p. 1101.
Mao, M.J., et al., "Oral administration of dextromethorphan prevents the development of morphine tolerance and dependence in rats," *Pain*, 1996, 67, 361-368.
Nichols, M.L., et al., "Enhancement of the antiallodynic and antinociceptive efficacy of spinal morphine by antisera to dynorphin A (1-13) or MK-801 in a nerve-ligation model of peripheral neuropathy," *Pain*, 1997, 69, 317-322.
Orchin, et al., The Vocabulary of Organic Chemistry, *John Wiley & Sons, Inc.*, 1981, p. 126.
Reisine, T., et al., "Opioid analgesics and antagonists," *Goodman & Gilman's the Pharmacological Basis of Therapeutics*, 9$^{th}$ Ed., 1996, 521-555.
Resnick, J., "Delayed gastric emptying and postoperative Ileus after nongastric abdominal surgery: Part 1," *Am. J. of Gastroenterology*, 1997, 92(5), 751-762.
Resnick, J., "Delayed gastric emptying and postoperative Ileus after nongastric abdominal surgery: Part II," *Am. J. of Gastroenterology*, 1997, 92(6), 934-940.

(Continued)

*Primary Examiner* — David J Blanchard
*Assistant Examiner* — Helen Chui
(74) *Attorney, Agent, or Firm* — Dechert LLP

(57) ABSTRACT

Methods of preventing and treating gastrointestinal dysfunction, particularly postoperative ileus and post-partum ileus, in a patient undergoing surgery or other biological stress by administering 4-aryl-piperidine derivatives are disclosed.

6 Claims, 2 Drawing Sheets

(56) References Cited

OTHER PUBLICATIONS

Schang, J.C., et al., "Beneficial effects of naloxone in a patient with intestinal pseudoobstruction," *Am. J. Gastroenerol.,* 1985, 80(6), 407-411.

Schuller, A.G.P., et al., "M6G, but not morphine, inhibits GI transit in MU opoid receptor deficient mice," *Society of Neuroscience Abstracts,* 1998, 24, p. 524.

Wittert, G., et al., "Tissue distribution of opioid receptor gene expression in the rat," *Biochem. and Biophys. Res. Commun.,* 1996, 218, 877-881.

Zimmerman, D.M., et al., "Discovery of a potent, peripherally selective *trans*-3,4-dimethyl-4-(3-hydroxyphenyl)piperidine opioid antagonist for the treatment of gastrointestinal motility disorders," *J. Med. Chem.,* 1994, 37, 2262-2265.

\* cited by examiner

METHODS OF PREVENTING AND TREATING GASTROINTESTINAL DYSFUNCTION

CROSS REFERENCE TO RELATED APPLICATIONS

This application claims benefit of U.S. Application No. 60/526,851 filed Dec. 4, 2003, the entire disclosure of which is incorporated herein by reference.

FIELD OF THE INVENTION

The present invention generally relates to methods of preventing and treating gastrointestinal (GI) dysfunction. More specifically, the present invention relates to methods of preventing and treating gastrointestinal dysfunction, particularly postoperative ileus and post-partum ileus, in a patient undergoing surgery or other biological stress, by administering 4-aryl-piperidine derivatives.

BACKGROUND OF THE INVENTION

It is well known that opioid drugs target three types of endogenous opioid receptors (i.e., $\mu$, $\delta$, $\kappa$ receptors) in biological systems. Many opiates, such as morphine, are mu opioid agonists that are often used as analgesics for the treatment of severe pain due to their activation of mu opioid receptors in the brain and central nervous system (CNS). Opioid receptors are, however, not limited to the CNS, and may be found in other tissues throughout the body. A number of side effects of opioid drugs may be caused by activation of these peripheral receptors. For example, administration of mu opioid agonists often results in intestinal dysfunction due to the large number of receptors in the wall of the gut (Wittert, G., Hope, P. and Pyle, D., *Biochemical and Biophysical Research Communications*, 1996, 218, 877-881; Bagnol, D., Mansour, A., Akil, A. and Watson, S. J., *Neuroscience*, 1997, 81, 579-591). Specifically, opioids are generally known to cause nausea and vomiting as well as inhibition of normal propulsive gastrointestinal function in animals and man (Reisine, T., and Pasternak, G., *Goodman & Gilman's The Pharmacological Basis of Therapeutics Ninth Edition*, 1996, 521-555) resulting in side effects such as, for example, constipation.

Recent evidence has indicated that naturally occurring endogenous opioid compounds may also affect propulsive activity in the gastrointestinal (GI) tract. Met-enkephalin, which activates mu and delta receptors in both the brain and gut, is one of several neuropeptides found in the GI tract (Koch, T. R., Carney, J. A., Go, V. L., and Szurszewski, J. H., *Digestive Diseases and Sciences*, 1991, 36, 712-728). Additionally, receptor knockout techniques have shown that mice lacking mu opioid receptors may have faster GI transit times than wild-type mice, suggesting that endogenous opioid peptides may tonically inhibit GI transit in normal mice (Schuller, A. G. P., King, M., Sherwood, A. C., Pintar, J. E., and Pasternak, G. W., *Society of Neuroscience Abstracts*, 1998, 24, 524). Studies have shown that opioid peptides and receptors located throughout the GI tract may be involved in normal regulation of intestinal motility and mucosal transport of fluids in both animals and man (Reisine, T., and Pasternak, G., *Goodman & Gilman's The Pharmacological Basis of Therapeutics Ninth Edition*, 1996, 521-555). Other studies show that the sympathetic nervous system may be associated with endogenous opioids and control of intestinal motility (Bagnol, D., Herbrecht, F., Jule, Y., Jarry, T., and Cupo, A., *Regul. Pept.*, 1993, 47, 259-273). The presence of endogenous opioid compounds associated with the GI tract suggests that an abnormal physiological level of these compounds may lead to bowel dysfunction.

It is a common problem for patients having undergone surgical procedures, especially surgery of the abdomen, to suffer from a particular bowel dysfunction called post-surgical (or postoperative) ileus. "ileus," as used herein, refers to the obstruction of the bowel or gut, especially the colon. See, e.g., *Dorland's Illustrated Medical Dictionary*, p. 816, 27th ed. (W.B. Saunders Company, Philadelphia 1988). Ileus should be distinguished from constipation, which refers to infrequent or difficulty in evacuating the feces. See, e.g., *Dorland's Illustrated Medical Dictionary*, p. 375, 27th ed. (W.B. Saunders Company, Philadelphia 1988). Ileus may be diagnosed by the disruption of normal coordinated movements of the gut, resulting in failure of the propulsion of intestinal contents. See, e.g., Resnick, *J. Am. J. of Gastroenterology*, 1992, 751 and Resnick, *J. Am. J. of Gastroenterology*, 1997, 92, 934. In some instances, particularly following surgery, including surgery of the abdomen, the bowel dysfunction may become quite severe, lasting for more than a week and affecting more than one portion of the GI tract. This condition is often referred to as post-surgical (or postoperative) paralytic ileus and most frequently occurs after laparotomy (see Livingston, E. H. and Passaro, E. D. Jr., *Digestive Diseases and Sciences*, 1990, 35, 121). Similarly, post-partum ileus is a common problem for women in the period following childbirth, and is thought to be caused by similar fluctuations in natural opioid levels as a result of birthing stress.

Gastrointestinal dysmotility associated with post-surgical ileus is generally most severe in the colon and typically lasts for 3 to 5 days. The administration of opioid analgesics to a patient after surgery may often contribute to bowel dysfunction, thereby delaying recovery of normal bowel function. Since virtually all patients receive opioid analgesics, such as morphine or other narcotics for pain relief after surgery, particularly major surgery, current post-surgical pain treatment may actually slow recovery of normal bowel function, resulting in a delay in hospital discharge and increasing the cost of medical care.

Post-surgical ileus may also occur in the absence of exogenous opioid agonists. It would be of benefit to inhibit the natural activity of endogenous opioids during and/or after periods of biological stress, such as surgery and childbirth, so that ileus and related forms of bowel dysfunction can be prevented or treated. Currently, therapies for ileus include functional stimulation of the intestinal tract, stool softeners, laxatives, lubricants, intravenous hydration, and nasogastric decompression. These prior art methods suffer from drawbacks, for example, as lacking specificity for post-surgical or post-partum ileus. And these prior art methods offer no means for prevention. If ileus could be prevented, hospital stays, recovery times, and medical costs would be significantly decreased in addition to the benefit of minimizing patient discomfort. Thus, drugs which selectively act on opioid receptors in the gut would be ideal candidates for preventing and/or treating post-surgical and post-partum ileus. Of those, drugs that do not interfere with the effects of opioid analgesics in the CNS would be of special benefit in that they may be administered simultaneously for pain management with limited side effects.

Peripheral opioid antagonists that do not cross the blood-brain barrier into the CNS are known in the literature and have been tested in relation to their activity on the GI tract. In U.S. Pat. Nos. 5,250,542, 5,434,171, 5,159,081, and 5,270,328, peripherally selective piperidine-N-alkylcarboxylate opioid antagonists are described as being useful in the treatment of idiopathic constipation, irritable bowel syndrome and opioid-induced constipation. Also, U.S. Pat. No. 4,176,186 describes quaternary derivatives of noroxymorphone (i.e., methylnaltrexone) that are said to prevent or relieve the intestinal immobility side-effect of narcotic analgesics without reducing analgesic effectiveness. U.S. Pat. No. 5,972,954 describes the use of methylnaltrexone, enteric-coated methylnaltrexone, or other quaternary derivatives of noroxymorphone for preventing and/or treating opioid- and/or non-opioid-induced side effects associated with opioid administration.

General opioid antagonists, such as naloxone and naltrexone have also been implicated as being useful in the treatment of GI tract dysmotility. For example, U.S. Pat. No. 4,987,126 and Kreek, M. J. Schaefer, R. A., Hahn, E. F., Fishman, J., *Lancet*, 1983, 1(8319), 261 disclose naloxone and other morphinan-based opioid antagonists (i.e., naloxone, naltrexone) for the treatment of idiopathic gastrointestinal dysmotility. In addition, naloxone has been shown to effectively treat non-opioid induced bowel obstruction, implying that the drug may act directly on the GI tract or in the brain (Schang, J. C., Devroede, G., *Am. J. Gastroenerol.*, 1985, 80(6), 407). Furthermore, it has been implicated that naloxone may provide therapy for paralytic ileus (Mack, D. J. Fulton, J. D., *Br. J. Surg.*, 1989, 76(10), 1101). However, it is well known that activity of naloxone and related drugs is not limited to peripheral systems and may interfere with the analgesic effects of opioid narcotics.

Inasmuch as post-surgical and post-partum ileus, for example, are common illnesses that add to the cost of health care and as yet have no specific treatments, there is a need for a specific and effective remedy. The majority of currently known opioid antagonist therapies are not peripherally selective and have the potential for undesirable side effects resulting from penetration into the CNS. Given the estimated 21 million inpatient surgeries and 26 outpatient surgeries each year, and an estimate of 4.7 million patients experiencing post-surgical ileus, methods involving opioid antagonists that are not only specific for peripheral systems, but specific for the gut, are desirable for treating post-surgical and post-partum ileus.

Alvimopan is an orally active, gastrointestinal (GI) restricted µ opioid antagonist being developed to alleviate the GI side effects associated with narcotic therapy. This compound differs from previously characterized peripherally selective opioid antagonists by its potency and degree of peripheral receptor selectivity [Zimmerman et al., *J. Med. Chem.*, 1994, 37, 2262-2265].

In clinical trials, alvimopan had heretofore been administered at least two hours prior to a surgical procedure to block the undesirable effects of opioid analgesics on the GI tract. Oftentimes, however, there may be insufficient time to administer the alvimopan at least two hours prior to surgery, especially prior to emergency surgery.

Therefore, it would be desirable to provide methods for preventing and/or treating gastrointestinal dysfunction, particularly postoperative ileus, in a patient undergoing surgery. The methods of the present invention are directed toward these, as well as other, important ends.

SUMMARY OF THE INVENTION

The methods of the present invention are directed to treating and preventing gastrointestinal dysfunction, particularly postoperative ileus and postpartum ileus, in a patient undergoing surgery or other biological stress.

In a first aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the free concentration in the plasma of said patient of said 4-aryl-piperidine derivative or stereoisomer, prodrug, pharmaceutically acceptable salt, hydrate, solvate, acid salt hydrate, N-oxide or isomorphic crystalline form thereof is sufficient to substantially saturate the µ opioid receptors in the gastrointestinal tract of said patient;

wherein said gastrointestinal dysfunction is postoperative ileus; and wherein said 4-aryl-piperidine derivative is [[2-[[4-(3-hydroxyphenyl)-3,4-dimethylpiperidin-1-yl]methyl]-3-phenylpropanoyl]amino]acetic acid.

In a second aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the plasma or whole blood concentration of said 4-aryl-piperidine derivative or stereoisomer, prodrug, pharmaceutically acceptable salt, hydrate, solvate, acid salt hydrate, N-oxide or isomorphic crystalline form thereof reaches a maximum concentration from about 30 minutes to about 120 minutes prior to said surgery;

wherein said gastrointestinal dysfunction is postoperative ileus; and wherein said 4-aryl-piperidine derivative is [[2-[[4-(3-hydroxyphenyl)-3,4-dimethylpiperidin-1-yl]methyl]-3-phenylpropanoyl]amino]acetic acid.

In a third aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the plasma or whole blood concentration of said 4-aryl-piperidine derivative or stereoisomer, prodrug, pharmaceutically acceptable salt, hydrate, solvate, acid salt hydrate, N-oxide or isomorphic crystalline form thereof reaches a maximum concentration from about 30 minutes to about 120 minutes after said administration;

wherein said gastrointestinal dysfunction is postoperative ileus; and wherein said 4-aryl-piperidine derivative is [[2-[[-4-(3-hydroxyphenyl)-3,4-dimethylpiperidin-1-yl]methyl]-3-phenylpropanoyl]amino]acetic acid.

In a fourth aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the free concentration in the plasma of said patient said 4-aryl-piperidine derivative or stereoisomer, prodrug, pharmaceutically acceptable salt, hydrate, solvate, acid salt hydrate, N-oxide or isomorphic crystalline form thereof is sufficient to substantially saturate the μ opioid receptors in the gastrointestinal tract of said patient;

wherein said gastrointestinal dysfunction is postoperative ileus; and wherein said 4-aryl-piperidine derivative is a compound of formula (IA):

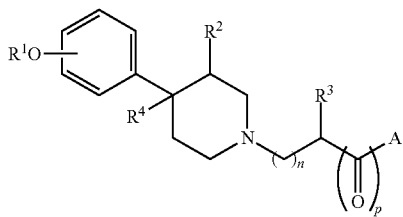

IA wherein:
$R^1$ is hydrogen or alkyl;
$R^2$ is hydrogen, alkyl, or alkenyl;
$R^3$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl;
$R^4$ is hydrogen, alkyl, or alkenyl;
A is $OR^5$ or $NR^6R^7$;
$R^5$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
$R^6$ is hydrogen or alkyl;
$R^7$ is hydrogen, alkyl, alkenyl, cycloalkyl, aryl, cycloalkyl-substituted alkyl, cycloalkenyl, cycloalkenyl-substituted alkyl, aralkyl, heteroaryl, heteroarylalkyl, B, or alkylene substituted B or, together with the nitrogen atom to which they are attached, $R^6$ and $R^7$ form a heterocyclic ring;
B is

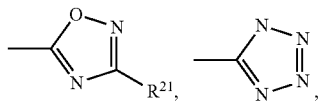

C(=O)W or $NR^8R^9$;
$R^8$ is hydrogen or alkyl;
$R^9$ is hydrogen, alkyl, alkenyl, cycloalkyl-substituted alkyl, cycloalkyl, cycloalkenyl, cycloalkenyl-substituted alkyl, aryl, aralkyl, heteroaryl, or heteroarylalkyl or, together with the nitrogen atom to which they are attached, $R^8$ and $R^9$ form a heterocyclic ring;
W is $OR^{10}$, $NR^{11}R^{12}$, or OE;
$R^{10}$ is hydrogen, alkyl, alkenyl, cycloalkyl, cycloalkenyl, cycloalkyl-substituted alkyl, cycloalkenyl-substituted alkyl, or aralkyl;
$R^{11}$ is hydrogen or alkyl;
$R^{12}$ is hydrogen, alkyl, alkenyl, aryl, cycloalkyl, cycloalkenyl, cycloalkyl-substituted alkyl, cycloalkenyl-substituted alkyl, aralkyl, heteroaryl, heteroarylalkyl, or alkylene substituted C(=O)Y or, together with the nitrogen atom to which they are attached, $R^{11}$ and $R^{12}$ form a heterocyclic ring;

E is

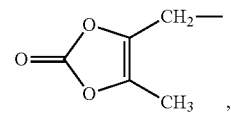

alkylene substituted (C=O)D, or $-R^{13}OC(=O)R^{14}$;
$R^{13}$ is alkyl substituted alkylene;
$R^{14}$ is alkyl;
D is $OR^{15}$ or $NR^{16}R^{17}$;
$R^{15}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
$R^{16}$ is hydrogen, alkyl, alkenyl, aryl, aralkyl, heteroaryl, heteroarylalkyl, cycloalkyl, cycloalkenyl, cycloalkyl-substituted alkyl or cycloalkenyl-substituted alkyl;
$R^{17}$ is hydrogen or alkyl or, together with the nitrogen atom to which they are attached, $R^{16}$ and $R^{17}$ form a heterocyclic ring;
Y is $OR^{18}$ or $NR^{19}R^{20}$;
$R^{18}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
$R^{19}$ is hydrogen or alkyl;
$R^{20}$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl or, together with the nitrogen atom to which they are attached, $R^{19}$ and $R^{20}$ form a heterocyclic ring;
$R^{21}$ is hydrogen or alkyl;
n is 0 to 4; and
p is 0 or 1.

In a fifth aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the plasma or whole blood concentration of said 4-aryl-piperidine derivative or stereoisomer, prodrug, pharmaceutically acceptable salt, hydrate, solvate, acid salt hydrate, N-oxide or isomorphic crystalline form thereof reaches a maximum concentration from about 30 minutes to about 120 minutes prior to said surgery;

wherein said gastrointestinal dysfunction is postoperative ileus; and wherein said 4-aryl-piperidine derivative is a compound of formula (IA):

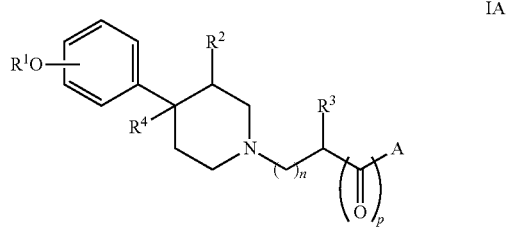

IA wherein:
$R^1$ is hydrogen or alkyl;
$R^2$ is hydrogen, alkyl, or alkenyl;

$R^3$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl;

$R^4$ is hydrogen, alkyl, or alkenyl;

A is $OR^5$ or $NR^6R^7$;

$R^5$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;

$R^6$ is hydrogen or alkyl;

$R^7$ is hydrogen, alkyl, alkenyl, cycloalkyl, aryl, cycloalkyl-substituted alkyl, cycloalkenyl, cycloalkenyl-substituted alkyl, aralkyl, heteroaryl, heteroarylalkyl, B, or alkylene substituted B or, together with the nitrogen atom to which they are attached, $R^6$ and $R^7$ form a heterocyclic ring;

B is

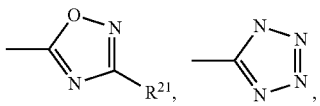

$C(=O)W$ or $NR^8R^9$;

$R^8$ is hydrogen or alkyl;

$R^9$ is hydrogen, alkyl, alkenyl, cycloalkyl-substituted alkyl, cycloalkyl, cycloalkenyl, cycloalkenyl-substituted alkyl, aryl, aralkyl, heteroaryl, or heteroarylalkyl or, together with the nitrogen atom to which they are attached, $R^8$ and $R^9$ form a heterocyclic ring;

W is $OR^{10}$, $NR^{11}R^{12}$, or OE;

$R^{10}$ is hydrogen, alkyl, alkenyl, cycloalkyl, cycloalkenyl, cycloalkyl-substituted alkyl, cycloalkenyl-substituted alkyl, or aralkyl;

$R^{11}$ is hydrogen or alkyl;

$R_{12}$ is hydrogen, alkyl, alkenyl, aryl, cycloalkyl, cycloalkenyl, cycloalkyl-substituted alkyl, cycloalkenyl-substituted alkyl, aralkyl, heteroaryl, heteroarylalkyl, or alkylene substituted $C(=O)Y$ or, together with the nitrogen atom to which they are attached, $R^{11}$ and $R^{12}$ form a heterocyclic ring;

E is

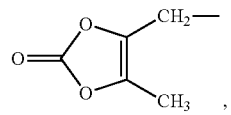

alkylene substituted $(C=O)D$, or $-R^{13}OC(=O)R^{14}$;

$R^{13}$ is alkyl substituted alkylene;

$R^{14}$ is alkyl;

D is $OR^{15}$ or $NR^{16}R^{17}$;

$R^{15}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;

$R^{16}$ is hydrogen, alkyl, alkenyl, aryl, aralkyl, heteroaryl, heteroarylalkyl, cycloalkyl, cycloalkenyl, cycloalkyl-substituted alkyl or cycloalkenyl-substituted alkyl;

$R^{17}$ is hydrogen or alkyl or, together with the nitrogen atom to which they are attached, $R^{16}$ and $R^{17}$ form a heterocyclic ring;

Y is $OR^{18}$ or $NR^{19}R^{20}$;

$R^{18}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;

$R^{19}$ is hydrogen or alkyl;

$R^{20}$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl or, together with the nitrogen atom to which they are attached, $R^{19}$ and $R^{20}$ form a heterocyclic ring;

$R^{21}$ is hydrogen or alkyl;

n is 0 to 4; and p is 0 or 1.

In a sixth aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the plasma or whole blood concentration of said 4-aryl-piperidine derivative or stereoisomer, prodrug, pharmaceutically acceptable salt, hydrate, solvate, acid salt hydrate, N-oxide or isomorphic crystalline form thereof reaches a maximum concentration from about 30 minutes to about 120 minutes after said administration;

wherein said gastrointestinal dysfunction is postoperative ileus; and wherein said 4-aryl-piperidine derivative is a compound of formula (IA):

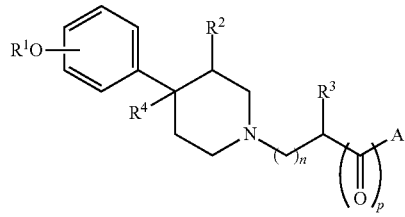

IA wherein:

$R^1$ is hydrogen or alkyl;

$R^2$ is hydrogen, alkyl, or alkenyl;

$R^3$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl;

$R^4$ is hydrogen, alkyl, or alkenyl;

A is $OR^5$ or $NR^6R^7$;

$R^5$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;

$R^6$ is hydrogen or alkyl;

$R^7$ is hydrogen, alkyl, alkenyl, cycloalkyl, aryl, cycloalkyl-substituted alkyl, cycloalkenyl, cycloalkenyl-substituted alkyl, aralkyl, heteroaryl, heteroarylalkyl, B, or alkylene substituted B or, together with the nitrogen atom to which they are attached, $R^6$ and $R^7$ form a heterocyclic ring;

B is

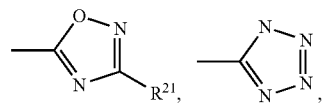

$C(=O)W$ or $NR^8R^9$;

$R^8$ is hydrogen or alkyl;

$R^9$ is hydrogen, alkyl, alkenyl, cycloalkyl-substituted alkyl, cycloalkyl, cycloalkenyl, cycloalkenyl-substituted alkyl, aryl, aralkyl, heteroaryl, or heteroarylalkyl or, together with the nitrogen atom to which they are attached, $R^8$ and $R^9$ form a heterocyclic ring;

W is $OR^{10}$, $NR^{11}R^{12}$, or OE;

$R^{10}$ is hydrogen, alkyl, alkenyl, cycloalkyl, cycloalkenyl, cycloalkyl-substituted alkyl, cycloalkenyl-substituted alkyl, or aralkyl;

$R^{11}$ is hydrogen or alkyl;

$R^{12}$ is hydrogen, alkyl, alkenyl, aryl, cycloalkyl, cycloalkenyl, cycloalkyl-substituted alkyl, cycloalkenyl-substituted alkyl, aralkyl, heteroaryl, heteroarylalkyl, or alkylene substituted C(=O)Y or, together with the nitrogen atom to which they are attached, $R^{11}$ and $R^{12}$ form a heterocyclic ring;

E is

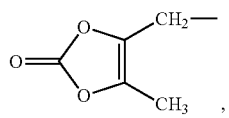

alkylene substituted (C=O)D, or —$R^{13}OC(=O)R^{14}$;

$R^{13}$ is alkyl substituted alkylene;

$R^{14}$ is alkyl;

D is $OR^{15}$ or $NR^{16}R^{17}$;

$R^{15}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;

$R^{16}$ is hydrogen, alkyl, alkenyl, aryl, aralkyl, heteroaryl, heteroarylalkyl, cycloalkyl, cycloalkenyl, cycloalkyl-substituted alkyl or cycloalkenyl-substituted alkyl;

$R^{17}$ is hydrogen or alkyl or, together with the nitrogen atom to which they are attached, $R^{16}$ and $R^{17}$ form a heterocyclic ring;

Y is $OR^{18}$ or $NR^{19}R^{20}$;

$R^{18}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;

$R^{19}$ is hydrogen or alkyl;

$R^{20}$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl or, together with the nitrogen atom to which they are attached, $R^{19}$ and $R^{20}$ form a heterocyclic ring;

$R^{21}$ is hydrogen or alkyl;

n is 0 to 4; and p is 0 or 1.

These and other aspects of the invention will become more apparent from the following detailed description.

DETAILED DESCRIPTION OF THE INVENTION

Figure 1:
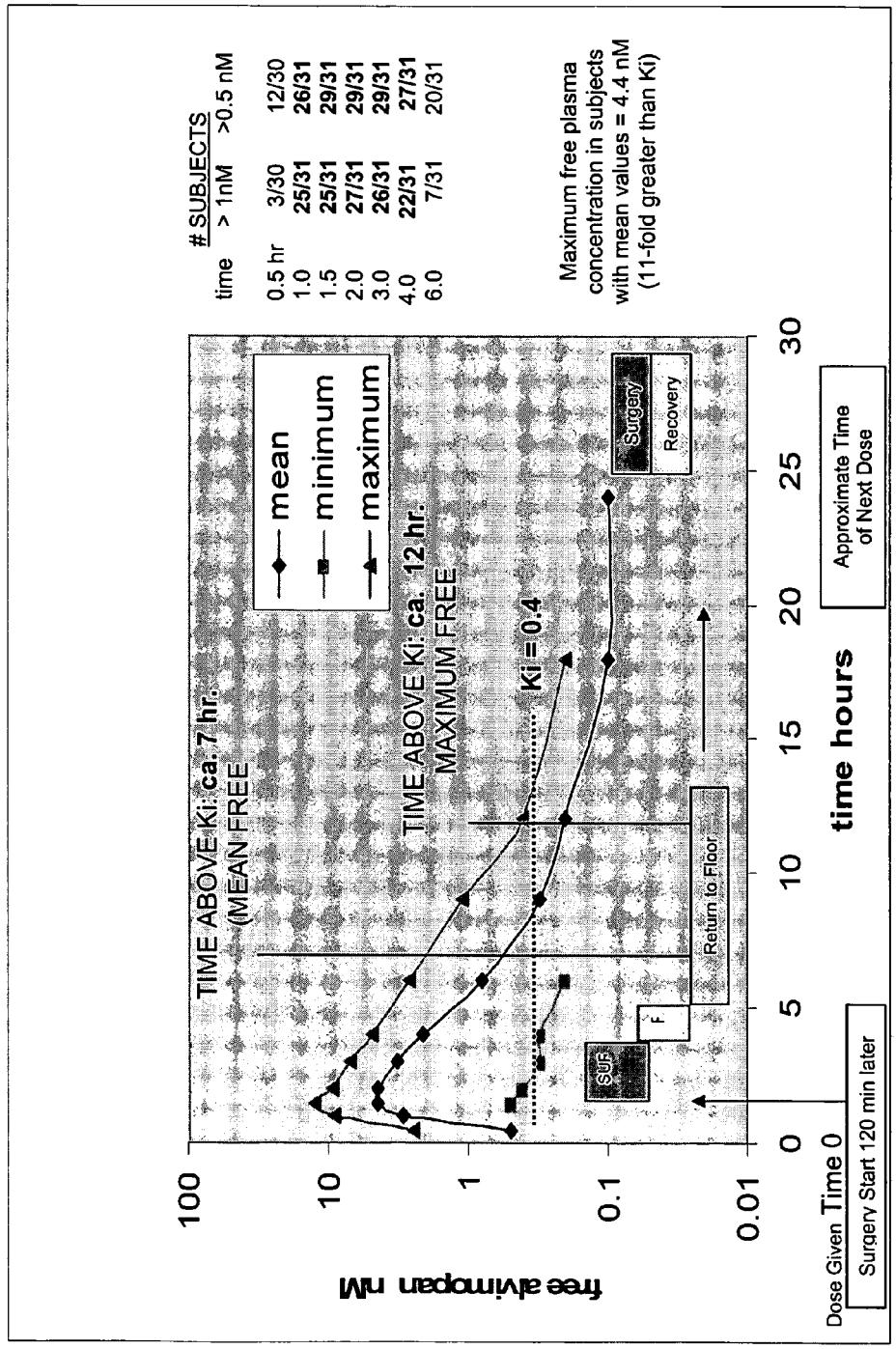
FIG. 1 shows the free plasma concentration of alvimopan (12 mg dose) as a function of time.

The methods of the present invention are directed to treating and preventing gastrointestinal dysfunction, particularly postoperative ileus and post-partum ileus, in a patient undergoing surgery. Different types of ileus may be treated and/or prevented using the methods of the present invention. The present methods are particularly suitable for treating and/or preventing postoperative ileus and post-partum ileus. "Postoperative ileus," which may follow surgery such as laparotomy, may be characterized by such symptoms as, for example, obstruction of the gut, particularly in the colon, resulting in nausea, vomiting, lack of passage of flatus and/or stools, abdominal distention and lack of bowel sounds. This condition generally lasts from about 3 to about 5 days, but may endure longer, including up to about one week. Longer durations are generally characteristic of a more severe form of ileus, termed post-surgical paralytic ileus, which may affect other portions of the GI tract in addition to the colon. "Postpartum ileus" generally refers to obstruction of the gut, particularly the colon, following parturition. Both natural and surgically-assisted procedures during parturition may lead to post-partum ileus treated by the present invention. Symptoms of post-partum ileus and postoperative ileus are similar.

As employed above and throughout the disclosure, the following terms, unless otherwise indicated, shall be understood to have the following meanings.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. "Branched" refers to an alkyl group in which a lower alkyl group, such as methyl, ethyl, or propyl, is attached to a linear alkyl chain. In certain preferred embodiments, the alkyl group is a $C_1$-$C_5$ alkyl group, i.e., a branched or linear alkyl group having from 1 to about 5 carbons. In other preferred embodiments, the alkyl group is a $C_1$-$C_3$ alkyl group, i.e., a branched or linear alkyl group having from 1 to about 3 carbons. Exemplary alkyl groups include methyl, ethyl, n-propyl, isopropyl, butyl, isobutyl, sec-butyl, tert-butyl, pentyl, hexyl, heptyl, octyl, nonyl, and decyl. "Lower alkyl" refers to an alkyl group having 1 to about 6 carbon atoms. Preferred alkyl groups include the lower alkyl groups of 1 to about 3 carbons. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkylene" refers to a bivalent alkyl radical having the general formula —$(CH_2)_n$—, where n is 1 to 10, and all combinations and subcombinations of ranges therein. The alkylene group may be straight, branched or cyclic. Non-limiting examples include methylene, methylene (—$CH_2$—), ethylene (—$CH_2CH_2$—), propylene (—$(CH_2)_3$—), trimethylene, pentamethylene, and hexamethylene. There may be optionally inserted along the alkylene group one or more oxygen, sulfur or optionally substituted nitrogen atoms, wherein the nitrogen substituent is alkyl as described previously. Alkylene groups can be optionally substituted. The term "lower alkylene" herein refers to those alkylene groups having from about 1 to about 6 carbon atoms. Preferred alkylene groups have from about 1 to about 4 carbons.

As used herein, "aralkylene" refers to a bivalent alkyl radical having the general formula —$(CH_2)_n$—, wherein any one of the hydrogens on the alkylene radical is replaced by an aryl group, and where n is 1 to 10. Aralkylene groups can be optionally substituted. Non-limiting examples include phenylmethylene, 2-phenyltrimethylene, 3-(p-anisyl)-pentamethylene, and 2-(m-trifluromethylphenyl)-hexamethylene.

Aralkylene groups can be substituted or unsubstituted. The term "lower aralkylene" herein refers to those aralkylene groups having from about 1 to about 6 carbon atoms in the alkylene portion of the aralkylene group.

As used herein, "alkenyl" refers to a monovalent alkyl radical containing at least one carbon-carbon double bond and having from 2 to about 10 carbon atoms in the chain, and all combinations and subcombinations of ranges therein. Alkenyl groups can be optionally substituted. In certain preferred embodiments, the alkenyl group is a $C_2$-$C_{10}$ alkyl group, i.e., a branched or linear alkenyl group having from 2 to about 10 carbons. In other preferred embodiments, the alkenyl group is a $C_2$-$C_6$ alkenyl group, i.e., a branched or linear alkenyl group having from 2 to about 6 carbons. In still other preferred embodiments, the alkenyl group is a $C_3$-$C_{10}$ alkenyl group, i.e., a branched or linear alkenyl group having from about 3 to about 10 carbons. In yet other preferred embodiments, the alkenyl group is a $C_2$-$C_5$ alkenyl group, i.e., a branched or linear alkenyl group having from 2 to about 5 carbons. Exemplary alkenyl groups include, for example, vinyl, propenyl, butenyl, pentenyl hexenyl, heptenyl, octenyl, nonenyl and decenyl groups.

As used herein, the term "alkenylene" refers to an alkylene group containing at least one carbon-carbon double bond. Exemplary alkenylene groups include, for example, ethenylene (—CH=CH—) and propenylene (—CH=CHCH$_2$—). Preferred alkenylene groups have from 2 to about 4 carbons.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "aralkyl" refers to alkyl radicals bearing an aryl substituent and have from about 6 to about 50 carbon atoms (and all combinations and subcombinations of ranges and specific numbers of carbon atoms therein), with from about 6 to about 10 carbon atoms being preferred. Aralkyl groups can be optionally substituted in either the aryl or alkyl portions. Non-limiting examples include, for example, phenylmethyl (benzyl), diphenylmethyl, triphenylmethyl, phenylethyl, diphenylethyl and 3-(4-methylphenyl)propyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred, with from about 3 to about 8 carbon atoms being more preferred, with from about 3 to about 6 carbon atoms being even more preferred. Multi-ring structures may be bridged or fused ring structures. The cycloalkyl group may be optionally substituted with, for example, alkyl, preferably $C_1$-$C_3$ alkyl, alkoxy, preferably $C_1$-$C_3$ alkoxy, or halo. Non-limiting examples include, for example, cyclopropyl, cyclobutyl, cyclopentyl, cyclohexyl, cycloheptyl cyclooctyl, and adamantyl.

As used herein, "cycloalkyl-substituted alkyl" refers to a linear alkyl group, preferably a lower alkyl group, substituted at a terminal carbon with a cycloalkyl group, preferably a $C_3$-$C_8$ cycloalkyl group. Non-limiting examples include, for example, cyclohexylmethyl, cyclohexylethyl, cyclopentylethyl, cyclopentylpropyl, cyclopropylmethyl and the like.

As used herein, "cycloalkenyl" refers to an olefinically unsaturated cycloalkyl group having from about 4 to about 10 carbons, and all combinations and subcombinations of ranges therein. In preferred embodiments, the cycloalkenyl group is a $C_5$-$C_8$ cycloalkenyl group, i.e., a cycloalkenyl group having from about 5 to about 8 carbons.

As used herein, "alkylcycloalkyl" refers to an optionally substituted ring system comprising a cycloalkyl group having one or more alkyl substituents. Non-limiting examples include, for example, alkylcycloalkyl groups include 2-methylcyclohexyl, 3,3-dimethylcyclopentyl, trans-2,3-dimethylcyclooctyl, and 4-methyldecahydronaphthalenyl.

As used herein, "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. The heterocycloalkyl group may be unsaturated, and may also be fused to aromatic rings. Non-limiting examples include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydrocyclopenta[c]pyranyl, 1,2,3,4,-tetrahydroquinolyl, octahydro-[2]pyrindinyl, decahydro-cycloocta[c]furanyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro[4.7]dodecane.

As used herein, the term "alkoxy" refers to an optionally substituted alkyl-O-group wherein alkyl is as previously defined. Non-limiting examples include, for example, include methoxy, ethoxy, n-propoxy, i-propoxy, n-butoxy, and heptoxy.

As used herein, the term "aryloxy" refers to an optionally substituted aryl-O-group wherein aryl is as previously defined. Non-limiting examples include, for example, phenoxy and naphthoxy.

As used herein, the term "aralkoxy" refers to an optionally substituted aralkyl-O-group wherein aralkyl is as previously defined. Non-limiting examples include, for example, benzyloxy, 1-phenylethoxy, 2-phenylethoxy, and 3-naphthylheptoxy.

As used herein, the term "aryloxyaryl" refers to an aryl group with an aryloxy substituent wherein aryloxy and aryl are as previously defined. Aryloxyaryl groups can be optionally substituted. Non-limiting examples include, for example, phenoxyphenyl, and naphthoxyphenyl.

As used herein, the term "heteroarylaryl" refers to an aryl group with a heteroaryl substituent wherein heteroaryl and aryl are as previously defined. Heteroarylaryl groups can be optionally substituted. Non-limiting examples include, for example, 3-pyridylphenyl, 2-quinolylnaphthalenyl, and 2-pyrrolylphenyl.

As used herein, the term "alkoxyaryl" refers to an aryl group bearing an alkoxy substituent wherein alkoxy and aryl are as previously defined. Alkoxyaryl groups can be optionally substituted. Non-limiting examples include, for example, para-anisyl, meta-t-butoxyphenyl, and methylendioxyphenyl.

As used herein, the term "carbon chain of said alkoxy interrupted by a nitrogen atom" refers to a carbon chain of an alkoxy group, wherein a nitrogen atom has been inserted between two adjacent carbon atoms of the carbon chain and wherein alkoxy is as previously defined. Both the alkoxy group and the nitrogen atom can be optionally substituted. Exemplary groups include —OCH$_2$CH$_2$N(CH$_3$)CH$_2$CH$_3$ and —OCH$_2$CH$_2$NHCH$_3$.

As used herein, the term "heterocycloalkylheteroaryl" refers to an heteroaryl group with a heterocycloalkyl substituent wherein heterocycloalkyl and heteroaryl are as previously defined. Heterocycloalkylheteroaryl groups can be optionally substituted. Exemplary heterocycloalkylheteroaryl groups include 3-[N-morpholinyl]pyridine and 3-[2-piperidinyl]pyridine.

As used herein, the term "heteroarylheteroaryl" refers to a heteroaryl group with a heteroaryl substituent wherein heteroaryl is as previously defined. Heteroarylherteroaryl groups can be optionally substituted. Exemplary heteroarylheteroaryl groups include 4-[3-pyridyl]pyridine and 2-[2-quinolyl]quinuclidine.

As used herein, the term "aralkoxyaryl" refers to an aryl group with an aralkoxy substituent wherein aralkoxy and aryl are as previously defined. Aralkoxyaryl groups can be optionally substituted. Exemplary aralkoxyaryl groups include benzyloxyphenyl and meta-toluenyloxyphenyl.

As used herein, the term "arylheteroaryl" refers to a heteroaryl group with an aryl substituent wherein aryl and heteroaryl are as previously defined. Arylheteroaryl groups can be optionally substituted. Exemplary arylheteroaryl groups include 3-phenylpyridyl and 2-naphthalenylquinolinyl.

As used herein, the term "alkoxyheteroaryl" refers to an heteroaryl group with an alkoxy substituent wherein alkoxy and heteroaryl are as previously defined. Alkoxyheteroaryl groups can be optionally substituted. Exemplary alkoxyheteroaryl groups include 2-methoxypyridine and 6-n-propoxyquinoline.

As used herein, "bicycloalkyl" refers to an optionally substituted, alkyl group having two bridged rings in its structure and having from about 7 to about 20 carbon atoms (and all combinations and subcombinations of ranges and specific numbers of carbon atoms therein), with from about 7 to about 15 carbon atoms being preferred. Exemplary bicycloalkyl-ring structures include, but are not limited to, norbornyl, bornyl, [2.2.2]-bicyclooctyl, cis-pinanyl, trans-pinanyl, camphanyl, iso-bornyl, and fenchyl.

As used herein, "bicycloalkenyl" refers to an optionally substituted, alkenyl group having two bridged rings in its structure and having from about 7 to about 20 carbon atoms (and all combinations and subcombinations of ranges and specific numbers of carbon atoms therein), with from about 7 to about 15 carbon atoms being preferred. Exemplary bicycloalkenyl-ring structures include, but are not limited to, bicyclo[2.2.1]hept-5-en-2-yl, bornenyl, [2.2.2]-bicyclooct-5-en-2-yl, α-pinenyl, β-pinenyl, camphenyl, and fenchyl.

As used herein, "carboxy" refers to a —C(=O)OH group.

As used herein, "alkanoyl" refers to a —C(=O)-alkyl group, wherein alkyl is as previously defined. Exemplary alkanoyl groups include acetyl (ethanoyl), n-propanoyl, n-butanoyl, 2-methylpropanoyl, n-pentanoyl, 2-methylbutanoyl, 3-methylbutanoyl, 2,2-dimethylpropanoyl, heptanoyl, decanoyl, and palmitoyl.

As used herein, "alkoxy-alkyl" refers to an alkyl-O-alkyl group where alkyl is as previously described.

As used herein, "heterocyclic" refers to a monocyclic or multicyclic ring system carbocyclic radical containing from about 4 to about 10 members, and all combinations and subcombinations of ranges therein, wherein one or more of the members is an element other than carbon, for example, nitrogen, oxygen or sulfur. The heterocyclic group may be aromatic or nonaromatic. Non-limiting examples include, for example, pyrrole and piperidine groups.

As used herein, "halo" refers to fluoro, chloro or bromo.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), carboxyl (—COOH), —C(=O)R", —OR", —C(=O)OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH$_2$, S(=O)$_2$NHR", S(=O)$_2$NR"R", NHS(=O)$_2$R", NR"S(=O)$_2$R", CF$_3$, CF$_2$CF$_3$, NHC(=O)NHR", NHC(=O)NR"R", NR"C(=O)NHR", NR"C(=O)NR"R", NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, the phrase "to substantially saturate" refers to the providing sufficient compound to the patient to achieve a maximum free (unbound) concentrations greater than or equal to 10-fold above the Ki to produce greater than 91% receptor occupancy, as defined in Copeland, R. E., *Enzymes. A Practical Introduction to Structure, Mechanism, and Data Analysis*, 2$^{nd}$ Edition, (New York: Wiley-VCH, 2000), page 88, the disclosure of which is incorporated herein by reference.

As used herein, the term "surgery" refers to any methodical action of the hand, or of the hand with instruments, on a patient, to produce a curative or remedial effect, and specifically includes Caesarian births and sterilizations.

As used herein, the term "side effect" refers to a consequence other than the one(s) for which an agent or measure is used, as the adverse effects produced by a drug, especially on a tissue or organ system other then the one sought to be benefited by its administration. In the case, for example, of the treatment of gastrointestinal dysfunction, such as the treatment of postoperative ileus, the term "side effect" may refer to such conditions as, for example, nausea, vomiting, diarrhea, and combinations thereof.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

As used herein, "patient" refers to animals, including mammals, preferably humans.

As used herein, "prodrug" refers to compounds specifically designed to maximize the amount of active species that reaches the desired site of reaction that are of themselves typically inactive or minimally active for the activity desired, but through biotransformation are converted into biologically active metabolites.

As used herein, "stereoisomers" refers to compounds that have identical chemical constitution, but differ as regards the arrangement of the atoms or groups in space.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, "hydrate" refers to a compound of the present invention which is associated with water in the molecular form, i.e., in which the H—OH bond is not split, and may be represented, for example, by the formula $R.H_2O$, where R is a compound of the invention. A given compound may form more than one hydrate including, for example, monohydrates ($R.H_2O$) or polyhydrates ($R.nH_2O$ wherein n is an integer >1) including, for example, dihydrates ($R.2H_2O$), trihydrates ($R.3H_2O$), and the like, or hemihydrates, such as, for example, $R.n/2H_2O$, $R.n/3H_2O$, $R.n/4H_2O$ and the like wherein n is an integer.

As used herein, "solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n (solvent)) wherein n is an integer >1) including, for example, disolvates (R.2(solvent)), trisolvates (R.3(solvent)), and the like, or hemisolvates, such as, for example, R.n/2(solvent), R.n/3(solvent), R.n/4(solvent) and the like wherein n is an integer. Solvents herein include mixed solvents, for example, methanol/water, and as such, the solvates may incorporate one or more solvents within the solvate.

As used herein, "acid salt hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

When any variable occurs more than one time in any constituent or in any formula, its definition in each occurrence is independent of its definition at every other occurrence. Combinations of substituents and/or variables are permissible only if such combinations result in stable compounds.

The piperidines derivatives useful in the methods of the invention as illustrated in formula (IA) can occur as the trans and cis stereochemical isomers at the 3- and 4-positions of the piperidine ring. The term "trans" as used herein refers, for example, in formula (IA) to the $R^2$ substituent being on the opposite side of the $R^4$ substituent, whereas in the "cis" isomer, the $R^2$ substituent and the $R^4$ substituent are on the same side of the ring. The present invention contemplates the individual stereoisomers, as well as racemic mixtures. In the most preferred compounds of formula (IA), the $R^2$ substituent and the $R^4$ substituent are in the "trans" orientation on the piperidine.

In addition to the "cis" and "trans" orientation of the $R^2$ substituent and the $R^4$ substituent of formula (IA), the absolute stereochemistry of the carbon atoms bearing $R^2$ substituent and the $R^4$ substituent of formula (IA) is also defined as using the commonly employed "R" and "S" definitions (Orchin et al., *The Vocabulary of Organic Chemistry*, John Wiley and Sons, Inc., 1981, page 126, which is incorporated herein by reference). The preferred compounds of the present invention are in which the configuration of both the R substituent and the $R^4$ substituents of formula (IA) on the piperidine ring are "R."

Furthermore, asymmetric carbon atoms may be introduced into the molecule depending on the structure of $R^4$. As such, these classes of compounds can exist as the individual "R" or "S" stereoisomers at these chiral centers, or the racemic mixture of the isomers, and all are contemplated as within the scope of the present invention. Preferably, a substantially pure stereoisomer of the compounds of this invention is used, i.e., an isomer in which the configuration at the chiral center is "R" or "S", i.e., those compounds in which the configuration at the three chiral centers are preferably 3R, 4R, S or 3R, 4R, R.

As used herein, "peripheral" or "peripherally-acting" refers to an agent that acts outside of the central nervous system.

As used herein, "centrally-acting" refers to an agent that acts within the central nervous system (CNS).

In certain preferred embodiments, the methods may involve a peripheral opioid antagonist compound. The term "peripheral" designates that the compound acts primarily on physiological systems and components external to the central nervous system. In preferred form, the peripheral opioid antagonist compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5% and most preferably 0% of the pharmacological activity of the compounds employed in the present methods is exhibited in the CNS.

Furthermore, it is preferred in certain embodiments of the invention that the compound of formula (IA) does not substantially cross the blood-brain barrier and thereby interfere with the receptors in the CNS. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier.

The methods of the present invention are directed to treating and preventing gastrointestinal dysfunction in a patient undergoing surgery or other biological stress, including the birth process. Such gastrointestinal dysfunction includes postoperative ileus and post-partum ileus.

The methods of the present invention may further employ one or more other active ingredients that may be conventionally employed in preventing or treating gastrointestinal dysfunction. Such conventional ingredients include, for example, laxatives, fiber, stool softeners, or bowel stimulants. Typical or conventional ingredients that may be included are described, for example, in the *Physicians' Desk Reference*, 2003, the disclosure of which is hereby incorporated herein by reference, in its entirety. Other optional components that may be employed in the methods and compositions of the present invention, in addition to those exemplified above, would be readily apparent to one of ordinary skill in the art, once armed with the teachings of the present disclosure.

Suitable 4-aryl-piperidine derivatives and a stereoisomer, a prodrug, a pharmaceutically acceptable salt, a hydrate, a solvate, an acid salt hydrate, an N-oxide and an isomorphic crystalline form thereof. Preferred 4-aryl-piperidine derivatives include, for example, the compounds disclosed in U.S. Pat. Nos. 5,250,542; 5,159,081; 5,270,328; and 5,434,171, 6,451,806 and 6,469,030, the disclosures of which are hereby incorporated herein by reference, in their entireties.

In a first aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the free concentration in the plasma of said patient of said 4-aryl-piperidine derivative or stereoisomer, prodrug, pharmaceutically acceptable salt, hydrate, solvate, acid salt hydrate, N-oxide or isomorphic crystalline form thereof is sufficient to substantially saturate the μ opioid receptors in the gastrointestinal tract of said patient;

wherein said gastrointestinal dysfunction is postoperative ileus; and wherein said 4-aryl-piperidine derivative is [[2-[[4-(3-hydroxyphenyl)-3,4-dimethylpiperidin-1-yl]methyl]-3-phenylpropanoyl]amino]acetic acid.

In a second aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the plasma or whole blood concentration of said 4-aryl-piperidine derivative or stereoisomer, prodrug, pharmaceutically acceptable salt, hydrate, solvate, acid salt hydrate, N-oxide or isomorphic crystalline form thereof reaches a maximum concentration from about 30 minutes to about 120 minutes prior to said surgery;

wherein said gastrointestinal dysfunction is postoperative ileus; and wherein said 4-aryl-piperidine derivative is [[2-[[4-(3-hydroxyphenyl)-3,4-dimethylpiperidin-1-yl]methyl]-3-phenylpropanoyl]amino]acetic acid.

In a third aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the plasma or whole blood concentration of said 4-aryl-piperidine derivative or stereoisomer, prodrug, pharmaceutically acceptable salt, hydrate, solvate, acid salt hydrate, N-oxide or isomorphic crystalline form thereof reaches a maximum concentration from about 30 minutes to about 120 minutes after said administration;

wherein said gastrointestinal dysfunction is postoperative ileus; and wherein said 4-aryl-piperidine derivative is [[2-[[4-(3-hydroxyphenyl)-3,4-dimethylpiperidin-1-yl]methyl]-3-phenylpropanoyl]amino]acetic acid.

In preferred embodiments, the [[2-[[4-(3-hydroxyphenyl)-3,4-dimethylpiperidin-1-yl]methyl]-3-phenylpropanoyl]amino]acetic acid is in hydrate form, more preferably, [[2-[[4-(3-hydroxyphenyl)-3,4-dimethylpiperidin-1-yl]methyl]-3-phenylpropanoyl]amino]acetic acid dihydrate, even more preferably in substantially pure isomeric form, most especially [[(2S)-2-[[(3R,4R)-4-(3-hydroxyphenyl)-3,4-dimethylpiperidin-1-yl]methyl]-3-phenylpropanoyl]amino]acetic acid dihydrate (alvimopan).

In a fourth aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the free concentration in the plasma of said patient of said 4-aryl-piperidine derivative or stereoisomer, prodrug, pharmaceutically acceptable salt, hydrate, solvate, acid salt hydrate, N-oxide or isomorphic crystalline form thereof is sufficient to substantially saturate the µ opioid receptors in the gastrointestinal tract of said patient;

wherein said gastrointestinal dysfunction is postoperative ileus; and wherein said 4-aryl-piperidine derivative is a compound of formula (IA):

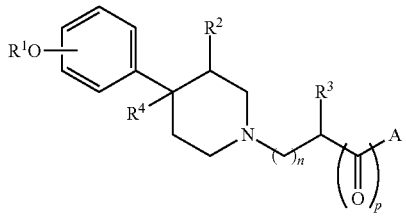

IA wherein:
$R^1$ is hydrogen or alkyl;
$R^2$ is hydrogen, alkyl, or alkenyl;
$R^3$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl;
$R^4$ is hydrogen, alkyl, or alkenyl;
A is $OR^5$ or $NR^6R^7$;
$R^5$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
$R^6$ is hydrogen or alkyl;
$R^7$ is hydrogen, alkyl, alkenyl, cycloalkyl, aryl, cycloalkyl-substituted alkyl, cycloalkenyl, cycloalkenyl-substituted alkyl, aralkyl, heteroaryl, heteroarylalkyl, B, or alkylene substituted B or, together with the nitrogen atom to which they are attached, $R^6$ and $R^7$ form a heterocyclic ring;
B is

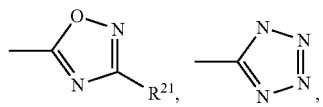

$C(=O)W$ or $NR^8R^9$;
$R^8$ is hydrogen or alkyl;
$R^9$ is hydrogen, alkyl, alkenyl, cycloalkyl-substituted alkyl, cycloalkyl, cycloalkenyl, cycloalkenyl-substituted alkyl, aryl, aralkyl, heteroaryl, or heteroarylalkyl or, together with the nitrogen atom to which they are attached, $R^8$ and $R^9$ form a heterocyclic ring;

W is $OR^{10}$, $NR^{11}R^{12}$, or OE;
$R^{10}$ is hydrogen, alkyl, alkenyl, cycloalkyl, cycloalkenyl, cycloalkyl-substituted alkyl, cycloalkenyl-substituted alkyl, or aralkyl;
$R^{11}$ is hydrogen or alkyl;
$R^{12}$ is hydrogen, alkyl, alkenyl, aryl, cycloalkyl, cycloalkenyl, cycloalkyl-substituted alkyl, cycloalkenyl-substituted alkyl, aralkyl, heteroaryl, heteroarylalkyl, or alkylene substituted $C(=O)Y$ or, together with the nitrogen atom to which they are attached, $R^{11}$ and $R^{12}$ form a heterocyclic ring;
E is

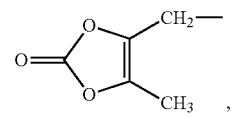

alkylene substituted $(C=O)D$, or $-R^{13}OC(=O)R^{14}$;
$R^{13}$ is alkyl substituted alkylene;
$R^{14}$ is alkyl;
D is $OR^{15}$ or $NR^{16}R^{17}$;
$R^{15}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
$R^{16}$ is hydrogen, alkyl, alkenyl, aryl, aralkyl, heteroaryl, heteroarylalkyl, cycloalkyl, cycloalkenyl, cycloalkyl-substituted alkyl or cycloalkenyl-substituted alkyl;
$R^{17}$ is hydrogen or alkyl or, together with the nitrogen atom to which they are attached, $R^{16}$ and $R^{17}$ form a heterocyclic ring;
Y is $OR^{18}$ or $NR^{19}R^{20}$;
$R^{18}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
$R^{19}$ is hydrogen or alkyl;
$R^{20}$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl or, together with the nitrogen atom to which they are attached, $R^{19}$ and $R^{20}$ form a heterocyclic ring;
$R^{21}$ is hydrogen or alkyl;
n is 0 to 4; and
p is 0 or 1.

In a fifth aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the plasma or whole blood concentration of said 4-aryl-piperidine derivative or stereoisomer, prodrug, pharmaceutically acceptable salt, hydrate, solvate, acid salt hydrate, N-oxide or isomorphic crystalline form thereof reaches a maximum concentration from about 30 minutes to about 120 minutes prior to said surgery;

wherein said gastrointestinal dysfunction is postoperative ileus; and wherein said 4-aryl-piperidine derivative is a compound of formula (IA):

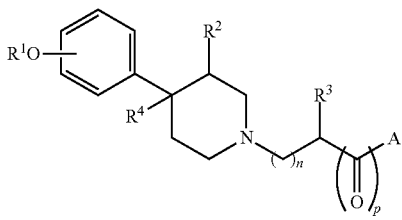

wherein:
R¹ is hydrogen or alkyl;
R² is hydrogen, alkyl, or alkenyl;
R³ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl;
R⁴ is hydrogen, alkyl, or alkenyl;
A is OR⁵ or NR⁶R⁷;
R⁵ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
R⁶ is hydrogen or alkyl;
R⁷ is hydrogen, alkyl, alkenyl, cycloalkyl, aryl, cycloalkyl-substituted alkyl, cycloalkenyl, cycloalkenyl-substituted alkyl, aralkyl, heteroaryl, heteroarylalkyl, B, or alkylene substituted B or, together with the nitrogen atom to which they are attached, R⁶ and R⁷ form a heterocyclic ring;
B is

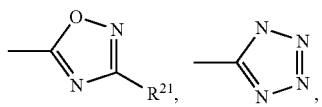

C(=O)W or NR⁸R⁹;
R⁸ is hydrogen or alkyl;
R⁹ is hydrogen, alkyl, alkenyl, cycloalkyl-substituted alkyl, cycloalkyl, cycloalkenyl, cycloalkenyl-substituted alkyl, aryl, aralkyl, heteroaryl, or heteroarylalkyl or, together with the nitrogen atom to which they are attached, R⁸ and R⁹ form a heterocyclic ring;
W is OR¹⁰, NR¹¹R¹², or OE;
R¹⁰ is hydrogen, alkyl, alkenyl, cycloalkyl, cycloalkenyl, cycloalkyl-substituted alkyl, cycloalkenyl-substituted alkyl, or aralkyl;
R¹¹ is hydrogen or alkyl;
R¹² is hydrogen, alkyl, alkenyl, aryl, cycloalkyl, cycloalkenyl, cycloalkyl-substituted alkyl, cycloalkenyl-substituted alkyl, aralkyl, heteroaryl, heteroarylalkyl, or alkylene substituted C(=O)Y or, together with the nitrogen atom to which they are attached, R¹¹ and R¹² form a heterocyclic ring;
E is

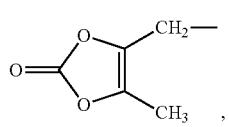

alkylene substituted (C=O)D, or —R¹³OC(=O)R¹⁴;
R¹³ is alkyl substituted alkylene;
R¹⁴ is alkyl;
D is OR¹⁵ or NR¹⁶R¹⁷;

R¹⁵ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
R¹⁶ is hydrogen, alkyl, alkenyl, aryl, aralkyl, heteroaryl, heteroarylalkyl, cycloalkyl, cycloalkenyl, cycloalkyl-substituted alkyl or cycloalkenyl-substituted alkyl;
R¹⁷ is hydrogen or alkyl or, together with the nitrogen atom to which they are attached, R¹⁶ and R¹⁷ form a heterocyclic ring;
Y is OR¹⁸ or NR¹⁹R²⁰;
R¹⁸ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
R¹⁹ is hydrogen or alkyl;
R₂₀ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl or, together with the nitrogen atom to which they are attached, R¹⁹ and R²⁰ form a heterocyclic ring;
R²¹ is hydrogen or alkyl;
n is 0 to 4; and
p is 0 or 1.

In a sixth aspect, the present invention is directed, in part, to methods of treating or preventing gastrointestinal dysfunction in a patient undergoing surgery, comprising the step of:

administering to said patient an effective amount of at least one 4-aryl-piperidine derivative or a stereoisomer, a prodrug, a pharmaceutically acceptable salt, a hydrate, a solvate, an acid salt hydrate, an N-oxide or an isomorphic crystalline form thereof;

in a manner so as to obtain a pharmacokinetic profile wherein the plasma or whole blood concentration of said 4-aryl-piperidine derivative or stereoisomer, prodrug, pharmaceutically acceptable salt, hydrate, solvate, acid salt hydrate, N-oxide or isomorphic crystalline form thereof reaches a maximum concentration from about 30 minutes to about 120 minutes after said administration;

wherein said gastrointestinal dysfunction is postoperative ileus; and wherein said 4-aryl-piperidine derivative is a compound of formula (IA):

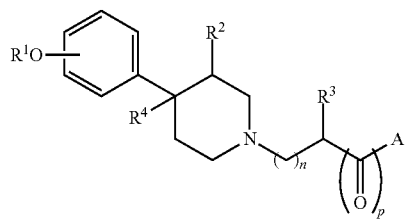

wherein:
R¹ is hydrogen or alkyl;
R² is hydrogen, alkyl, or alkenyl;
R³ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl;
R⁴ is hydrogen, alkyl, or alkenyl;
A is OR⁵ or NR⁶R⁷;
R⁵ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;
R⁶ is hydrogen or alkyl;

$R^7$ is hydrogen, alkyl, alkenyl, cycloalkyl, aryl, cycloalkyl-substituted alkyl, cycloalkenyl, cycloalkenyl-substituted alkyl, aralkyl, heteroaryl, heteroarylalkyl, B, or alkylene substituted B or, together with the nitrogen atom to which they are attached, $R^6$ and $R^7$ form a heterocyclic ring;

B is

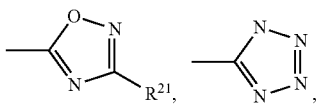

$C(=O)W$ or $NR^8R^9$;

$R^8$ is hydrogen or alkyl;

$R^9$ is hydrogen, alkyl, alkenyl, cycloalkyl-substituted alkyl, cycloalkyl, cycloalkenyl, cycloalkenyl-substituted alkyl, aryl, aralkyl, heteroaryl, or heteroarylalkyl or, together with the nitrogen atom to which they are attached, $R^8$ and $R^9$ form a heterocyclic ring;

W is $OR^{10}$, $NR^{11}R^{12}$, or OE;

$R^{10}$ is hydrogen, alkyl, alkenyl, cycloalkyl, cycloalkenyl, cycloalkyl-substituted alkyl, cycloalkenyl-substituted alkyl, or aralkyl;

$R^{11}$ is hydrogen or alkyl;

$R^{12}$ is hydrogen, alkyl, alkenyl, aryl, cycloalkyl, cycloalkenyl, cycloalkyl-substituted alkyl, cycloalkenyl-substituted alkyl, aralkyl, heteroaryl, heteroarylalkyl, or alkylene substituted $C(=O)Y$ or, together with the nitrogen atom to which they are attached, $R^{11}$ and $R^{12}$ form a heterocyclic ring;

E is

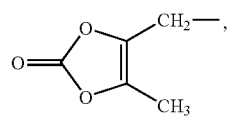

alkylene substituted (C=O)D, or $-R^{13}OC(=O)R^{14}$;

$R^{13}$ is alkyl substituted alkylene;

$R^{14}$ is alkyl;

D is $OR^{15}$ or $NR^{16}R^{17}$;

$R^{15}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;

$R^{16}$ is hydrogen, alkyl, alkenyl, aryl, aralkyl, heteroaryl, heteroarylalkyl, cycloalkyl, cycloalkenyl, cycloalkyl-substituted alkyl or cycloalkenyl-substituted alkyl;

$R^{17}$ is hydrogen or alkyl or, together with the nitrogen atom to which they are attached, $R^{16}$ and $R^{17}$ form a heterocyclic ring;

Y is $OR^{18}$ or $NR^{19}R^{20}$;

$R^{18}$ is hydrogen, alkyl, alkenyl, cycloalkyl, cycloalkenyl, cycloalkyl-substituted alkyl, cycloalkenyl-substituted alkyl, aralkyl, heteroaryl, or heteroarylalkyl;

$R^{19}$ is hydrogen or alkyl;

$R^{20}$ is hydrogen, alkyl, alkenyl, aryl, cycloalkyl, cycloalkenyl, cycloalkyl-substituted alkyl, cycloalkenyl-substituted alkyl, aralkyl, heteroaryl, or heteroarylalkyl or, together with the nitrogen atom to which they are attached, $R^{19}$ and $R^{20}$ form a heterocyclic ring;

$R^{21}$ is hydrogen or alkyl;

n is 0 to 4; and p is 0 or 1.

In preferred embodiments, the compound of formula (IA) is a trans 3,4-isomer.

In certain embodiments employing compounds of formula (IA), it is preferred that $R^1$ is hydrogen;

$R^2$ is alkyl;

n is 1 or 2;

$R^3$ is benzyl, phenyl, cyclohexyl, or cyclohexylmethyl; and $R^4$ is alkyl.

In certain embodiments employing compounds of formula (IA), it is preferred that A is $OR^5$; and $R^5$ is hydrogen or alkyl.

In certain embodiments employing compounds of formula (IA), it is preferred that A is $NR^6R^7$;

$R^6$ is hydrogen;

$R^7$ is alkylene substituted B; and

B is C(O)W.

In certain embodiments employing compounds of formula (IA), it is preferred that $R^7$ is $(CH_2)_q$—B;

q is about 1 to about 3;

W is $OR^{10}$; and $R^{10}$ is hydrogen, alkyl, phenyl-substituted alkyl, cycloalkyl or cycloalkyl-substituted alkyl.

In certain embodiments including compounds of formula (IA), it is preferred that W is $NR^{11}R^{12}$ $R^{11}$ is hydrogen or alkyl; and $R^{12}$ is hydrogen, alkyl or alkylene substituted $C(=O)Y$.

In certain embodiments employing compounds of formula (IA), it is preferred that $R^{12}$ is $(CH_2)_mC(O)Y$;

m is 1 to 3;

Y is $OR^{18}$ or $NR^{19}R^{20}$; and $R^{18}$, $R^{19}$ and $R^{20}$ are independently hydrogen or alkyl.

In certain embodiments employing compounds of formula (IA), it is preferred that W is OE;

E is $CH_2C(=O)D$;

D is $OR^{15}$ or $NR^{16}R^{17}$;

$R^{15}$ is hydrogen or alkyl;

$R^{16}$ is methyl or benzyl; and $R^{17}$ is hydrogen.

In certain embodiments employing compounds of formula (IA), it is preferred that W is OE;

E is $R^{13}OC(=O)R^{14}$;

$R^{13}$ is $-CH(CH_3)-$ or $-CH(CH_2CH_3)-$; and $R^{14}$ is alkyl.

In certain embodiments including compounds of formula (IA), it is preferred that p is 1.

In certain embodiments employing compounds of formula (IA), it is preferred that the configuration at positions 3 and 4 of the piperidine ring is each R.

Preferred compounds of formula (IA) include:

Q-$CH_2CH(CH_2(C_6H_5))C(O)OH$,

Q-$CH_2CH_2CH(C_6H_5)C(O)NHCH_2C(O)OCH_2CH_3$,

Q-$CH_2CH_2CH(C_6H_5)C(O)NHCH_2C(O)OH$,

Q-$CH_2CH_2CH(C_6H_5)C(O)NHCH_2C(O)NHCH_3$,

Q-$CH_2CH_2CH(C_6H_5)C(O)NHCH_2C(O)NHCH_2CH_3$,

G-$NH(CH_2)_2C(O)NH_2$,

G-$NH(CH_2)_2C(O)NHCH_3$,

G-$NHCH_2C(O)NH_2$,

G-$NHCH_2C(O)NHCH_3$,

G-$NHCH_2C(O)NHCH_2CH_3$,

G-$NH(CH_2)_3C(O)OCH_2CH_3$,

G-$NH(CH_2)_3C(O)NHCH_3$,

G-NH(CH$_2$)$_2$C(O)OH,
G-NH(CH$_2$)$_3$C(O)OH,
Q-CH$_2$CH(CH$_2$(C$_6$H$_{11}$))C(O)NHCH$_2$C(O)OH,
Q-CH$_2$CH(CH$_2$(C$_6$H$_{11}$))C(O)NH(CH$_2$)$_2$C(O)OH,
Q-CH$_2$CH(CH$_2$(C$_6$H$_{11}$))C(O)NH(CH$_2$)$_2$C(O)NH$_2$,
Z-NHCH$_2$C(O)OCH$_2$CH$_3$,
Z-NHCH$_2$C(O)OH,
Z-NHCH$_2$C(O)NH$_2$,
Z-NHCH$_2$C(O)N(CH$_3$)$_2$,
Z-NHCH$_2$C(O)NHCH(CH$_3$)$_2$,
Z-NHCH$_2$C(O)OCH$_2$CH(CH$_3$)$_2$,
Z-NH(CH$_2$)$_2$C(O)OCH$_2$(C$_6$H$_5$),
Z-NH(CH$_2$)C(O)OH,
Z-NH(CH$_2$)$_2$C(O)NHCH$_2$CH$_3$,
Z-NH(CH$_2$)$_3$C(O)NHCH$_3$,
Z-NHCH$_2$C(O)NHCH$_2$C(O)OH,
Z-NHCH$_2$C(O)OCH$_2$C(O)OCH$_3$,
Z-NHCH$_2$C(O)O(CH$_2$)$_4$CH$_3$,
Z-NHCH$_2$C(O)OCH$_2$C(O)NHCH$_3$,
Z-NHCH$_2$C(O)O-(4-methoxycyclohexyl),
Z-NHCH$_2$C(O)OCH$_2$C(O)NHCH$_2$(C$_6$H$_5$) and
Z-NHCH$_2$C(O)OCH(CH$_3$)OC(O)CH$_3$;
wherein:
Q represents

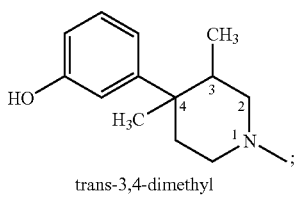 [SMILES: CC1CN(C)CCC1(C)c1cccc(O)c1]

trans-3,4-dimethyl

G represents

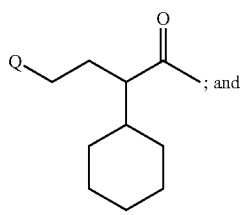

; and and
Z represents

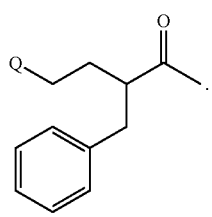

More preferred compounds of formula (IA) include:
(+)-Z-NHCH$_2$C(O)OH,
(−)-Z-NHCH$_2$C(O)OH,
(3R,4R)-Z-NHCH$_2$C(O)NHCH$_2$(C$_6$H$_5$) and
(3R,4R)-G-NH(CH$_2$)$_3$C(O)OH,
wherein Q, Z and G are as defined above.

Even more preferred compounds of formula (IA) include (+)-Z-NHCH$_2$C(O)OH and (−)-Z-NHCH$_2$C(O)OH, most especially (+)-Z-NHCH$_2$C(O)OH, where Z is as defined above.

Even more preferred compounds of formula (IA) include Q-CH$_2$CH(CH$_2$(C$_6$H$_5$))C(O)OH, wherein Q is as defined above. It is especially preferred when said compound is (3R, 4R,S)-Q-CH$_2$CH(CH$_2$(C$_6$H$_5$))C(O)OH.

A particularly preferred embodiment of the present invention is the compound (+)-Z-NHCH$_2$C(O)OH, i.e., the compound of the following formula (II):

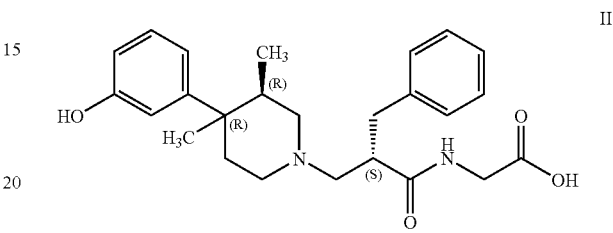

II

The compound of formula (II) has low solubility in water except at low or high pH conditions.

In especially preferred embodiments, the compound of a formula (IA) is a substantially pure stereoisomer.

In preferred embodiments, the methods may further comprise the step of administering at least one opioid to the patient. The opioid may be administered to the patient before, during, or after surgery or another biological stress. Suitable opioids include alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, and tramadol. Preferred opioids include morphine, codeine, oxycodone, hydrocodone, dihydrocodeine, propoxyphene, fentanyl, and tramadol.

The opioid component may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference,* 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J. et al., *Pain* 1996, 67, 361), L-364,718 and other CCK antagonists (Dourish, C. T. et al., *Eur. J. Pharmacol.,* 1988, 147, 469), NOS inhibitors (Bhargava, H. N. et al., *Neuropeptides,* 1996, 30, 219), PKC inhibitors (Bilsky, E. J. et al., *J. Pharmacol. Exp. Ther.* 1996, 277, 484), and dynorphin antagonists or antisera (Nichols, M. L. et al., *Pain,* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

In certain preferred embodiments, the 4-aryl-piperidine derivative or stereoisomer, prodrug, pharmaceutically acceptable salt, hydrate, solvate, acid salt hydrate, N-oxide or isomorphic crystalline form thereof is administered to the patient from about 30 minutes to less than about 120 minutes prior to the administration of the opioid (and all combinations and subcombinations of ranges and specific administration times therein), preferably from about 30 minutes to less than about 90 minutes prior to the administration of the opioid, more preferably from about 30 minutes to less than about 60 minutes prior to the administration of the opioid, and even more preferably from about 30 minutes to less than about 45 minutes prior to the administration of the opioid.

In certain preferred embodiments, the 4-aryl-piperidine derivative or stereoisomer, prodrug, pharmaceutically acceptable salt, hydrate, solvate, acid salt hydrate, N-oxide or isomorphic crystalline form thereof is administered to the patient from about 30 minutes to less than about 120 minutes prior to surgery (and all combinations and subcombinations of rangers and specific administration times therein), preferably from about 30 minutes prior to surgery to less than about 90 minutes prior to surgery, more preferably from about 30 minutes prior to surgery to less than about 60 minutes prior to surgery, and even more preferably from about 30 minutes prior to surgery to less than about 45 minutes prior to surgery.

In certain preferred embodiments, the 4-aryl-piperidine derivative or stereoisomer, prodrug, pharmaceutically acceptable salt, hydrate, solvate, acid salt hydrate, N-oxide or isomorphic crystalline form thereof is administered to the patient orally.

In certain other preferred embodiments, the 4-aryl-piperidine derivative or stereoisomer, prodrug, pharmaceutically acceptable salt, hydrate, solvate, acid salt hydrate, N-oxide or isomorphic crystalline form thereof is administered to the patient parenterally, more preferably intravenously.

The compounds employed in the methods of the present invention may exist in prodrug form. As used herein, "prodrug" is intended to include any covalently bonded carriers that release the active parent drug, for example, as according to formulas (IA) or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula (IA), may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, using the methods described in U.S. Pat. Nos. 5,250,542, 6,469,030, and 6,451,806, the disclosures of which are hereby incorporated by reference, in their entireties. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

As noted above, the compounds of the present invention can exist as the individual stereoisomers. Preferably, reaction conditions are adjusted as disclosed in U.S. Pat. No. 4,581,456 or as set forth in Example 1 of U.S. Pat. No. 5,250,542 to be substantially stereoselective and provide a racemic mixture of essentially two enantiomers. These enantiomers may then be resolved. A procedure which may be employed to prepare the resolved starting materials used in the synthesis of these compounds includes treating a racemic mixture of alkyl-3,4-dimethyl-4-(3-alkoxyphenyl)piperidine with either (+)- or (−)-ditoluoyl tartaric acid to provide the resolved intermediate. This compound may then be dealkylated at the 1-position with vinyl chloroformate and finally converted to the desired 4-(3-hydroxyphenyl)piperidine isomer.

As will be understood by those skilled in the art, the individual enantiomers of the invention can also be isolated with either (+) or (−) dibenzoyl tartaric acid, as desired, from the corresponding racemic mixture of the compounds of the invention. Preferably, the (+)-trans enantiomer is obtained.

Although the (+)trans-3,4 stereoisomer is preferred, all of the possible stereoisomers of the compounds described herein are within the contemplated scope of the present invention. Racemic mixtures of the stereoisomers as well as the substantially pure stereoisomers are within the scope of the invention. The term "substantially pure," as used herein, refers to at least about 90 mole percent, more preferably at least about 95 mole percent and most preferably at least about 98 mole percent of the desired stereoisomer is present relative to other possible stereoisomers.

The compounds employed in the methods of the present invention may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which is hereby incorporated herein by reference, in its entirety.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, and intraperitoneal. Other acceptable routes of administration are transepithelial including transdermal, transnasal, ophthalmic, sublingual and buccal; topically including ophthalmic, dermal, ocular, and rectal; nasal or pulmonary inhalation via insufflation or aerosol; and rectal systemic.

The active compound may be orally administered, for example, with an inert diluent or with an assimilable edible carrier, it may be enclosed in hard or soft shell gelatin capsules, it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is from about 0.1 mg/day to about 500 mg/day of active compound, including all combinations, and subcombinations thereof.

In certain preferred embodiments of the invention, said 4-aryl-piperidine derivative or stereoisomer, prodrug, pharmaceutically acceptable salt, hydrate, solvate, acid salt hydrate, N-oxide or isomorphic crystalline form thereof is administered at a level of at least about 0.75 mg/day, more preferably at a level of at least about 1 mg/day, even more preferably at a level of at least about 2 mg/day, and yet even more preferably at a level of at least about 3 mg/day.

In certain preferred embodiments of the invention, said 4-aryl-piperidine derivative or stereoisomer, prodrug, pharmaceutically acceptable salt, hydrate, solvate, acid salt hydrate, N-oxide or isomorphic crystalline form thereof is administered at a level of less than about 300 mg/day, more preferably at a level of less than about 120 mg/day, even more preferably at a level of less than about 60 mg/day, and yet even more preferably at a level of less than about 30 mg/day.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze-drying technique that yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The combination products useful in the methods of this invention, such as pharmaceutical compositions comprising 4-aryl-piperidine derivatives with additional active ingredients, may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the 4-aryl-piperidine derivative and additional active ingredient may be administered at the same time or simultaneously (that is, together), or in any order. When not administered at the same time or simultaneously, that is, when administered sequentially, preferably the administration of a 4-aryl-piperidine derivative and additional active ingredient occurs less than about one hour apart, more preferably less than about 30 minutes apart, even more preferably less than about 15 minutes apart, and still more preferably less than about 5 minutes apart.

Preferably, administration of the combination products of the invention is oral or intravenously, although other routes of administration, as described above, are contemplated to be within the scope of the present invention. Although it is preferable that the 4-aryl-piperidine derivative and the additional active ingredients are all administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Particularly when provided as a single dosage form, the potential exists for a chemical interaction between the combined active ingredients. For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-pareils, which are then enteric coated. These enteric coated microtablets, particles, granules or non-pareils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in the methods of the invention are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The 4-aryl-piperidine derivative and the optional additional active ingredient may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

EXAMPLES

The present invention will now be illustrated by reference to the following specific, non-limiting examples. The examples are not intended to limit the scope of the present invention.

Example 1

Twelve milligrams of alvimopan (two 6 mg capsules) was administered orally to patients about 120 minutes prior to surgery. The free alvimopan plasma concentration was measured for about 24 hours. The results are shown in FIG. 1.

FIG. 1 shows the free plasma concentration of alvimopan (12 mg dose) (in nM) as a function of time (in hours). This figure shows that a single 12 mg oral dose of alvimopan produced free plasma concentrations sufficient to substantially saturate μ opioid receptors in the GI tract. Maximum concentrations achieved were 11-fold greater than the Ki. Moreover, the profile demonstrates that the Ki is exceeded at various times by a factor ranging from approximately 6 to twice the Ki; concentrations that would be estimated to produce receptor occupancy of greater than 68%, still within a reasonable interpretation of "substantial saturation."

Example 2

A randomized, double-blind, placebo-controlled study of different doses of alvimopan (opioid antagonist) I.V. for 4 days in the presence and absence of loperamide (opioid) 2 mg p.o. q.i.d. in 60 healthy subjects (n=12 in each of five treatment groups) was carried out. Subjects were randomly assigned to receive one of the following five treatments:
Group 1: Placebo for alvimopan I.V. b.i.d.+placebo for loperamide p.o. q.i.d. (n=12)
Group 2: Placebo for alvimopan I.V. b.i.d.+loperamide 2 mg p.o. q.i.d. (n=12)
Group 3: Alvimopan 1 mg I.V. b.i.d.+loperamide 2 mg p.o. q.i.d. (n=12)
Group 4: Alvimopan 0.45 mg I.V. b.i.d.+loperamide 2 mg p.o. q.i.d. (n=12)
Group 5: Alvimopan 0.1 mg I.V. b.i.d.+loperamide 2 mg p.o. q.i.d. (n=12)
Oral SITZMARKS capsules containing radio-opaque markers were be administered on Days 1, 2, and 3. Alvimopan and loperamide was administered at the same time, when applicable.

Study Assessments

Serial blood samples were collected for the determination of concentrations of alvimopan and its amide hydrolysis metabolite in plasma.

Subjects were assessed for their pain at the I.V. infusion site using a categorical four-point verbal scale (i.e., no discomfort/pain, mild discomfort/pain, moderate pain, or severe pain). The Investigator also assessed certain characteristics (e.g., erythema) of the I.V. site (i.e., none, mild, moderate, or severe). Abdominal x-rays and x-rays of stool samples were performed to determine the location of the SITZMARKS markers.

The appropriate dose was drawn into the delivery system, normal saline was added to bring the total volume to 6 mL, and the contents will be mixed thoroughly. Placebo for alvimopan I.V. was 6 mL of normal saline.

Alvimopan or matching placebo and loperamide or matching placebo were administered on Days 1 through 4. Note that only the morning doses of alvimopan and loperamide were administered on Day 4.

Oral SITZMARKS capsules were administered on Days 1, 2, and 3 at the same time that study medication is administered each day.

Pharmacokinetic Sampling

The first eight subjects in each treatment group followed a full sampling schedule and the last four subjects followed a sparse sampling schedule. For the first eight subjects (full sampling schedule), blood samples was collected just prior to administration of alvimopan I.V. on Days 1 through 4 (four samples); and at 0.5, 1, 1.5, 2, 5, 10, 20, 30, and 60 minutes and at 2, 4, 6, 8, 10, 12, 16, 24, 48, 72, 96, 120, 144, and 168 hours after the end of the infusion of alvimopan I.V. on Day 4. This is a total of 27 samples per subject (135 mL per subject).

For the last four subjects in each treatment group (sparse sampling schedule), blood was collected prior to administration of alvimopan I.V. on Days 1 through 4 (four samples), and immediately following the last infusion on Day 4. Subjects were randomized to have one sample collected during each of the following intervals, relative to the end of the infusion on Day 4:
Interval 1: 3, 5, 10, or 15 minutes
Interval 2: 1, 2, 2.5, or 3 hours
Interval 3: 4, 5, 6, or 8 hours
Interval 4: 10, 12, 14, or 16 hours
Interval 5: 24, 48, 72, or 96 hours
Interval 6: 120 or 144 hours
GI transit score (GITS) was measured by the transit of radio-opaque markers administered on Days 1,2 and 3 with an abdominal x-ray on Day 4.

Figure 2:
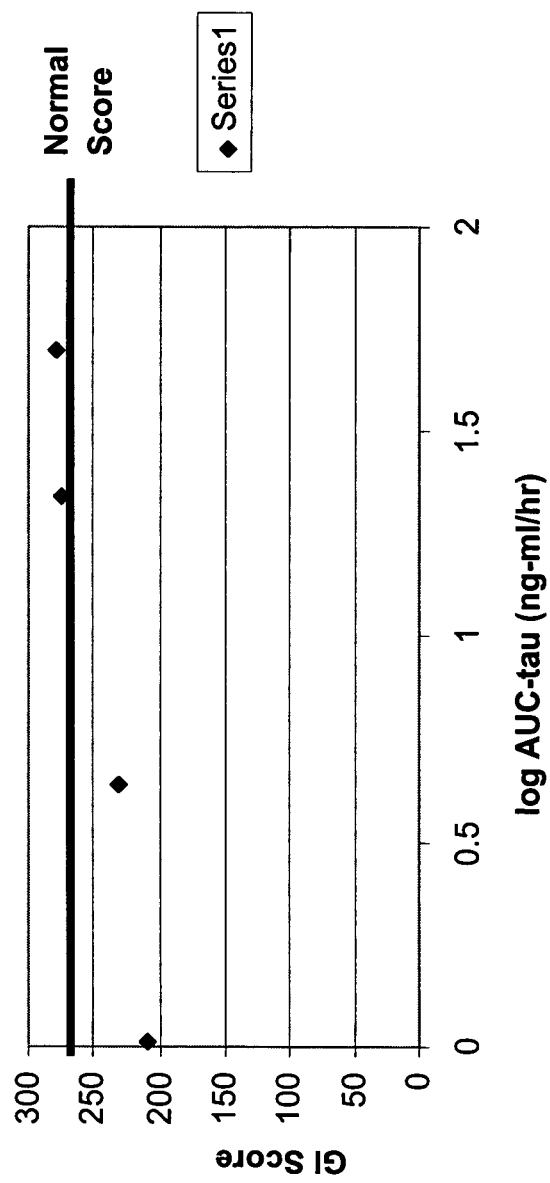
FIG. 2 shows GI score as a function of log of plasma concentrations measured as AUC (τ) (in ng-ml/hr) with a GI score measured by radio-opaque markers in subjects given loperamide with either placebo or one of three doses of I.V. alvimopan (0.1 mg b.i.d, 0.45 mg b.i.d., and 1 mg b.i.d.) selected to target different plasma concentrations (4.5, 20, and 45 ng/ml, respectively).

FIG. 2 shows GI score as a function of log of plasma concentrations measured as AUC (τ) (in ng-ml/hr) with a GI score measured by radio-opaque markers in subjects given loperamide with either placebo or one of three doses of I.V. alvimopan (0.1 mg b.i.d, 0.45 mg b.i.d., and 1 mg b.i.d.) selected to target different plasma concentrations (4.5, 20, and 45 ng/ml, respectively).

The means for the groups are:

| Group | AUC (τ) of Alvimopan (ng-ml/hr) | log AUC (τ) of Alvimopan (ng-ml/hr) | GI Score |
| --- | --- | --- | --- |
| 1 | 0 | — | 255.56 |
| 2 | 0 | — | 208.67 |
| 3 | 4.36 | 0.639486 | 231 |
| 4 | 22.06 | 1.343606 | 274.62 |
| 5 | 49.79 | 1.697142 | 278.5 |

The $R^2$ value for the means is 0.76. The normal GI score (no loperamide, no alvimopan) was 255.56. Groups 4 and 5 are statistically different from Group 2 and not different from normal (Group 1). This data suggests that that plasma concentrations are important in antagonizing the effect of opioids on GI transit. Further, the figures show that increasing exposure, as measured by AUC, which takes into account both concentration and time, produces an improved effect (antagonizing the effect of opioids on GI transit).

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:
1. A method of treating a gastrointestinal dysfunction in a patient undergoing surgery, comprising the step of:
orally administering to the patient from about 30 minutes prior to surgery to 60 minutes prior to surgery about 12 mg of a compound which is [[2-[[-4-(3-hydroxyphenyl)-3,4-dimethylpiperidin-1-yl]methyl]-3-phenylpropanoyl]amino]acetic acid or a pharmaceutically acceptable salt or hydrate thereof.

2. A method according to claim 1, wherein said compound is 2-[[(2S)-2-[[(3R,4R)-4-(3-hydroxyphenyl)-3,4-dimethylpiperidin-1-yl]methyl]-3-phenyl-propanoyl]amino]acetic acid dihydrate.

3. A method according to claim 2, wherein the surgery is abdominal surgery.

4. A method of claim 3, wherein the gastrointestinal dysfunction is postoperative ileus.

5. A method of claim 2, wherein the compound is administered to the patient from about 30 minutes prior to surgery to less than 60 minutes prior to surgery.

6. A method of claim 2, wherein the compound is administered to the patient from about 30 minutes prior to surgery to less than 45 minutes prior to surgery.

\* \* \* \* \*